United States Patent [19]
Novotny et al.

[11] Patent Number: 5,453,382
[45] Date of Patent: Sep. 26, 1995

[54] ELECTROCHROMATOGRAPHIC PRECONCENTRATION METHOD

[75] Inventors: Milos V. Novotny, Bloomington, Ind.; Takao Tsuda, Aichi, Japan; Helena A. Soini, Bloomington, Ind.

[73] Assignee: Indiana University Foundation, Bloomington, Ind.

[21] Appl. No.: 992,232

[22] Filed: Dec. 17, 1992

Related U.S. Application Data

[63] Continuation-in-part of Ser. No. 740,538, Aug. 5, 1991, abandoned.

[51] Int. Cl.[6] .......................... G01N 27/26; G01N 27/447
[52] U.S. Cl. .......................... 436/178; 436/161; 436/162; 204/180.1; 204/299 R; 73/23.39; 422/69; 422/70
[58] Field of Search ................ 73/23.39, 23.42; 204/180.1, 182.8, 183.3, 299 R; 422/69, 70; 436/92, 98, 161, 162, 178, 816, 901

[56] References Cited

U.S. PATENT DOCUMENTS

| | | | |
|---|---|---|---|
| 4,222,836 | 9/1980 | Kerr et al. | 204/180 G |
| 4,459,198 | 7/1984 | Mizuno et al. | 204/299 R |
| 5,340,452 | 8/1994 | Brenner et al. | 204/180.1 |

FOREIGN PATENT DOCUMENTS 0168957  5/1983  Japan.

OTHER PUBLICATIONS

Tsuda, "Chromatographic Behavior in Electrochromatography" *Anal. Chem*, 1988, 60, 1677–1680.

*Primary Examiner*—James C. Housel
*Assistant Examiner*—Harold Y. Pyon
*Attorney, Agent, or Firm*—Townsend and Townsend Khourie and Crew

[57] ABSTRACT

Solutions of analytes in concentrations too low for certain analytical techniques such as various capillary electrophoresis techniques are concentrated in a solid-phase adsorption medium by a technique which involves a pressure-gradient-driven adsorption of the analyte followed by a desorption of the analyte and its removal using electroosmotic bulk flow.

13 Claims, 7 Drawing Sheets

ELECTROCHROMATOGRAPHIC PRECONCENTRATION METHOD

GOVERNMENT RIGHTS

This invention was made at least in part with United States Government support under Grant No. GM24349, awarded by the National Institute of General Medical Sciences, U.S. Department of Health and Human Services. The United States Government has certain rights in this invention.

CROSS REFERENCE TO RELATED APPLICATION

This application is a continuation-in-part of application Ser. No. 07/740,538, filed Aug. 5, 1991, abandoned.

This invention lies in the fields of solute adsorption and electrochromatography. In particular, this invention is concerned with methods of preparing samples for electrochromatographic analyses using electromigration or chromatographic techniques.

BACKGROUND OF THE INVENTION

Capillary electrophoretic techniques have assumed ever increasing importance as an analytical method for the detection and quantitation of biological molecules. The small diameter of the capillary affords a high degree of temperature control which permits the use of high voltages, separating molecules from complex biological mixtures from which the molecules are not otherwise separable or detectable. The small sample size is also an advantage in many cases, but a disadvantage in others. When therapeutic drugs are present in very low concentrations, for example, highly sensitive detection techniques such as laser-induced fluorescence are required.

Problems have also been encountered in the isolation and detection of certain biological compounds of neutral character which are highly soluble in water, since these qualities make it difficult to separate these compounds by traditional chromatographic techniques. Prevailing methods involve laborious extractions prior to the analysis, but even these are unsuitable for chromatographic techniques since they result in a relatively dilute solution of the analyte, requiring solvent removal before such techniques as high performance liquid chromatography can be employed.

These and other problems are addressed by the present invention.

SUMMARY OF THE INVENTION

It has now been discovered that analytes in biological source solutions can be preconcentrated, and in certain cases purified, to raise the concentrations to a level suitable for analysis by capillary electrophoresis, by a technique involving the use of a solid-phase adsorption medium and a sequential combination of pressure-driven and electrically-driven flows. The source solution is applied to the adsorption medium in a first stage of the method, under conditions which promote the sorption of the analyte of interest by the solid-phase medium. Concentration of the analyte occurs in this stage either by the use of a large volume of sample relative to the adsorption medium, or by the concentration of the analyte in an inlet region of the medium, or by a combination of the two. In a second stage, the environment of the medium is changed to one which will promote the desorption of the analyte from the medium, and a voltage is impressed across the medium to induce electroosmosis. The bulk solvent flow caused by the electroosmotic effect transports the analyte in concentrated form out of the adsorption medium to a location where it can be collected and recovered for analysis by capillary electrophoresis or by any other form of analysis which uses small samples.

In preferred embodiments of the invention, the adsorption medium is a particulate material retained in a column. The analyte in these embodiments does not penetrate deeply into the column but instead becomes concentrated near the entry end of the column as the source solution is passed through the column. Desorption is then performed during electroosmotic flow in the opposite direction, resulting in the analyte leaving the medium at the same end at which it entered and thereby retaining the relatively high concentration which it achieved during adsorption by the column packing.

The change of conditions between the adsorption and desorption stages is generally achieved by a change in the mobile phase, such as for example from a polar to a non-polar phase, or vice versa, or a change in the degree of polarity. With certain analytes, the most appropriate and preferred condition for the adsorption phase is that of reverse phase chromatography, and the change in conditions is achieved by a change in solvents.

Other objects, advantages and features of the invention will become apparent from the description which follows.

BRIEF DESCRIPTION OF THE DRAWINGS

FIGS. 3A and 3B represent the prior art.

DETAILED DESCRIPTION OF THE INVENTION AND PREFERRED EMBODIMENTS

The adsorption medium used in the present invention may vary widely in both physical form and chemical composition. The optimum choice of medium for any particular source solution or analyte will depend on the analyte itself and whatever other solutes are present in the source solution. The choice of medium may also be affected by the size of the source solution and the concentration of the analyte in the source solution, as well as on the chromatographic method to be applied to the analyte after it has been eluted in concentrated form from the adsorption medium. With considerations such as these in mind, the adsorption medium will most likely be an immobile solid phase, and may for example assume the form of a coating on a surface such as the inner wall of a tube or the form of particles, beads or spheres in a packed bed. The adsorption medium will be retained in a receptacle which permits flowing through of the sample and of a wash solution and an elution buffer, preferably in either of two opposite directions. Accordingly, one preferred configuration of the adsorption medium is a packed bed retained in a flow-through column or cartridge.

The relative volumes of the adsorption medium and of the source solution to be passed through the adsorption medium in the first stage of the method of the invention may vary widely, and are not critical. It is desirable however to remove at least a portion of any additional, chromatographically interfering solutes present in the source solution, or at least to reduce the concentration of these extraneous solutes relative to the analyte of interest. One method of achieving this is by using a volume of source solution which is equal to or greater than the volume of adsorption medium through which the solution is passed. When a large volume of source solution is used relative to the adsorption medium, the analyte retained by the adsorption medium will occupy a volume considerably smaller than that of the source solution from which it was drawn, while the extraneous solutes are passed through the medium rather than being retained. The source solution itself will thus effectively prevent the extraneous solutes from accumulating in the adsorption medium. Alternatively, or in addition, a wash fluid may be passed through the adsorption medium subsequent to the source solution, preferably in the same direction, to remove the extraneous solutes or at least lower their concentration. Concentration of the analyte in the adsorption medium is further enhanced by the use of a flow-through column to retain the medium, such that upon introduction of the sample into the column, the analyte will penetrate only a short distance into the column, thereby becoming concentrated near the end where the sample was introduced. The concentration is maintained upon subsequent desorption by causing flow to occur in the opposite direction, thereby avoiding the need for the concentrated analyte to pass further into the column where zone spreading might occur. These methods may be used either individually or in combination to raise the concentration of the analyte relative to the source solution itself and to the concentrations of other extraneous solutes in the source solution.

The selection of adsorption medium, and hence the adsorption mechanism, may vary widely. Examples are various forms of specific and non-specific affinity chromatography, normal and reverse phase chromatography, hydrophobic interaction chromatography, and ion-exchange chromatography. For certain analytes, particularly those of a neutral character, reverse phase chromatography is of particular interest.

Bonded or surface-derivatized column packings are preferred. Examples of bonded phases are silicas bonded with non-polar groups such as octadecyl, octyl and other alkyl groups; polar groups such as cyanopropyl and other cyanoalkyl groups, and aminopropyl and other aminoalkyl groups; and ionizable groups such as sulphonic acid groups and quaternary ammonium groups. Supports other than silica may also be used. Included among these are a variety of commercially available synthetics and ceramics. In general, any support or adsorptive material which has previously been described for use in high performance liquid chromatography, thin-layer chromatography, or gas chromatography may be used.

Introduction of the source solution into the adsorption medium is achieved under conditions which will promote the immobilization of the analyte by the stationary phase. This is generally achieved by preconditioning of the stationary phase in terms of functional groups and by appropriate selection of a mobile phase in terms of such factors as polarity and ion content. In a preferred practice of the invention, the source solution is combined with a potion of the mobile phase prior to introduction into the column, and is passed through the column in this diluted form. In further preferred embodiments, the introduction of the sample is followed by the passage through the column of a wash solution to reduce the presence of extraneous solutes. The wash solution is either the same as, or similar in character to, the mobile phase in which the source solution was diluted, so that the same type of partitioning between mobile and stationary phases will occur in both the sample introduction and the wash step. Furthermore, as indicated above, the wash solution is preferably passed through the column in the same direction as the diluted source solution, to avoid any possibility of a loss of unadsorbed analyte from the column.

Passage of the source solution and the wash solution through the column are achieved by application of a pressure gradient across the column. This is achieved by conventional means, such as those used in conventional high-performance liquid chromatography. A voltage gradient is not necessary in this stage of the process, and the pressure gradient is preferably applied in the absence of a voltage gradient.

The desorption stage of the process of this invention includes convening the environment or condition of the adsorption medium to one which promotes desorption of the analyte, and effecting desorption by use of a voltage gradient in a manner which induces electroosmotic flow. The conversion of the medium is conveniently achieved by changing the mobile phase. The type of change in the mobile phase will vary depending on the type of adsorptive interaction by which the analyte is immobilized by the stationary phase. To achieve the change, the first stage mobile phase may be simply displaced by the second stage mobile phase before the electroosmotic flow is begun. Displacement may be achieved by a pressure gradient similar to the one used in the adsorption stage, although preferably in the opposite direction.

A type of change which is particularly effective in many situations is a shift in the degree of polarity of the mobile phase by the substitution of one solvent for another. In reverse phase chromatographic interactions, for example, the mobile phase used during the adsorption stage will preferably have a polarity which exceeds that of the stationary phase, i.e., the polarity of the adsorption medium will be substantially less than the polarity of the first mobile phase. The second mobile phase, which is used during the desorption stage, will then be one having a polarity substantially less than the polarity of the first mobile phase, thereby lowering the retention of the analyte by the adsorption medium. For example, with an analyte having a $pK_a$ of from about 6.5 to about 7.5, the preferred adsorption medium will be one having a surface with substantially non-polar functional groups, the first mobile phase will include a solvent or medium to high polarity, and the second mobile phase will include a solvent of low polarity, the terms "medium," "high" and "low" having meaning to those skilled in this art.

Examples of solvents of medium to high polarity are 2-methoxyethanol, acetonitrile, ethanol, methanol and water, while examples of solvents of low polarity are hexane, methylbenzene, tetrahydrofuran, trichloromethane, butanone, ethyl ethanoate, dichloromethane, 1,2-dichloroethane, propanone and 1,4-dioxane.

Mobilization in the desorption stage is achieved by electroosmotic flow induced by the application of a voltage across the medium. Electroosmotic flow is achieved by the use of a column which gives rise to an electrokinetic potential at its surface. The column in which the adsorption medium is retained, therefore, may have been partially derivatized with active sites remaining for the formation of electrokinetic potential, but has not been surface derivatized or otherwise treated in such fashion as to prevent the formation of an electrokinetic potential. Accordingly, the entire mobile phase will undergo bulk flow as a result of the applied voltage. The electroosmotic effect may be accompanied by electrophoretic mobility of the analyte and any other solutes present, but this is not required, and in preferred embodiments of the invention, the electroosmotic effect is at least equal to the electrophoretic effect and, in the most preferred embodiments, predominates. In the preferred practice of the invention, the voltage is applied in the absence of a pressure gradient, with the result that the electrical effects comprise the entire driving force, including the electroosmotic effect primarily together with any electrophoretic effect which is present as well.

The voltage used is not critical to the invention and may vary widely. Best results are generally obtained using voltages in the range of from about 30 V/cm to about 300 V/cm, preferably from about 75 V/cm to about 200 V/cm. The voltage may be applied by conventional means, preferably with direct current.

As indicated above, the desorption stage is preferably conducted in such a manner that flow is induced in the direction opposite the direction of flow during the adsorption stage. Thus, the polarity of the applied voltage is selected such that the electroosmotic flow moves toward the end of the column through which the source solution was introduced in the first stage. This is achieved by placing the negative electrode at the end of the column where the source solution and wash solution were introduced. Accordingly, when the second mobile phase is introduced into the system to displace the first mobile phase prior to application of the voltage, the introduction of the second mobile phase preferably occurs in the reverse direction as well, i.e., toward the end of the column through which the source solution was initially introduced.

In further preferred embodiments of the invention, buffers are included in the mobile phase. This is of particular utility in matching the mobile phase with the mobile phase to be used in the chromatographic analysis or with a buffer suitable for electrophoretic analysis, which is subsequently performed on the concentrated solution. The choice and amount of buffer will depend on the analyte and the analytic method to be used, as well as other factors relating to the types of interactions sought to be achieved in both the preconcentration and the analysis. Examples of buffers are conventional acetate, tartrate, phosphate, citrate, borate and barbital buffers, as well as 2-(N-morpholino)ethanesulfonic acid (MES), N-(2-acetamido)-2-aminoethanesulfonic acid (ACES), piperazine-N,N'-bis(2-ethanesulfonic acid) (PIPES), N,N-bis(2-hydroxyethyl)-2-aminoethanesulfonic acid (BES), N-2hydroxyethylpiperazine-N'-2-ethanesulfonic acid (HEPES), N-2-hydroxyethylpiperazine-N'-3-propanesulfonic acid (EPPS), N-tris(hydroxymethyl)methylglycine (tricine), N,N-bis(hydroxyethyl)glycine (bicine), tris(hydroxymethyl)aminomethane (Tris, "TRIZMA"), and tris(hydroxymethyl) methylaminopropane sulfonic acid (TAPS).

The method of the present invention may be applied to source solutions of a wide variety of sources and analyte concentrations. The invention will be of particular interest, however in the treatment of source solutions in which the analyte is present at concentrations of less than about 100 µg/mL, preferably less than about 50 µg/mL, and most preferably less than about 20 µg/mL. Source solutions of particular interest will be biological mixtures and fluids such as sera, plasma, cellular fluids and urine, as well as residential and commercial fluids such as drinking water, ground water and waste water. Applicability of the invention also extends to air contaminants which can be solubilized in liquid solvents.

Once the analyte has been concentrated by the methods described above, it is ready for analysis by any analytical method utilizing a small sample. Examples are capillary zone electrophoresis (CZE), micellar and other forms of electrokinetic capillary chromatography (MECC), isotachophoresis, isoelectric focusing, high performance liquid chromatography (HPLC), and non-capillary methods such as mass spectroscopy (MS). A sample of the concentrated analyte solution may be extracted from the first elution fraction emerging from the adsorption medium in the preconcentration method, and injected or otherwise applied to the analytical apparatus in the conventional manner. Alternatively, an on-line arrangement may be used, in which the column containing the adsorption medium is directly connected to the capillary or other apparatus in which the analysis will take place, injection being performed by the electroosmotic flow itself.

Figure 1:
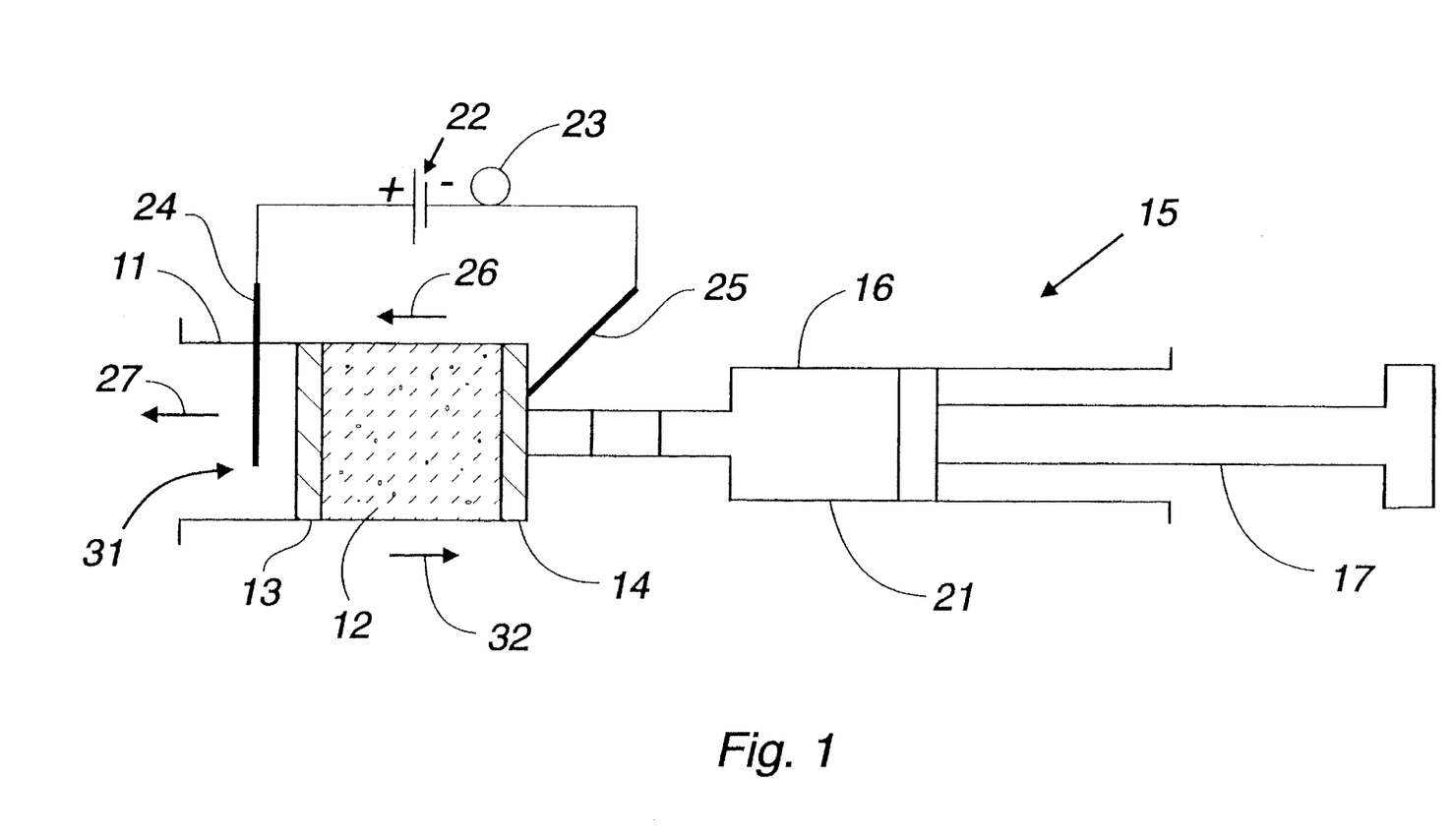
FIG. 1 is a cross-sectional view of a preconcentration tube for use in the practice of the present invention.

FIG. 1 is an illustration of apparatus in which the preconcentration method of the present invention may be performed. A solid-phase extraction tube 11 contains a packing material 12 held in place by porous polyethylene frits 13, 14. As an example of the dimensions which might actually bemused, the tube may have an internal diameter of 6 mm, and the length of the packing may be 0.8 era; and each frit may be 1 mm in thickness, with pores measuring 20 microns in diameter. The packing may be conventional C-18 packing, 40-micron particle size, 100 mg total.

Attached to one end of the extraction tube is a conventional syringe 15 having a syringe barrel 16 and plunger 17. Connecting the syringe barrel to the extraction tube is a connecting tube 21, which may for example be polypropylene with an inner diameter of 3 mm and an outer diameter of 6 min. The syringe 15 in this construction is used as a means of manually imposing a pressure gradient across the length of the extraction tube, in either direction. Any other conventional kind of pumping device may be substituted for the syringe. Voltage is supplied by is power supply 22, equipped with a current measurement device 23 and positive and negative electrodes 24, 25.

To operate the apparatus of FIG. 1 in the preconcentration of a selected analyte in a serum sample in accordance with the invention, the sample is first diluted with a mixture of buffer and solvent which will promote the adsorption of the analyte by the extraction tube packing, and placed in the syringe barrel 16. Also, the packing 12 in the extraction tube is preconditioned and activated, for example by equilibration with water, methanol, water again, and then the buffer. At this stage of the procedure, the power supply is not turned on. The syringe barrel 16 is then joined to the extraction tube 11 by the connecting tube 21, and the diluted serum sample is forced slowly through the packing in the direction shown by the arrow 26 by pushing in the plunger 17 (toward the left in the view shown in the Figure). The sample displaces the buffer in the packing, which leaves the extraction tube 11 at the left as waste 27. The syringe 15 is then separated from the connecting tube 21 and filled with water. The syringe 15 is then rejoined to the connecting tube, and 1.0 mL of water is pumped through the extraction tube 11, once again by pushing in the syringe plunger 16. The water travels through the extraction tube in the same direction as the sample.

What has up until this point been the discharge end 31 of the extraction tube 11 is now connected to a reservoir containing a solvent-buffer mixture which promotes the desorption of the analyte from the packing 12. The syringe plunger 17 is then extended (pulled to the right in the view shown in the Figure), causing the solvent-buffer mixture (tetrahydrofuran as the solvent, for example) to be drawn into the extraction tube in the direction shown by the arrow 32, displacing the water in the packing. In a typical experiment, this is achieved by drawing 160 µL of water into the syringe barrel.

The syringe is now removed and replaced with a collection tube (not shown). The power supply is then engaged, with the positive electrode 24 in the extraction tube to one side of the packing 12, and the negative electrode 25 touching the outside surface of the front frit 14. Sufficient voltage is applied to cause a fast electroosmotic bulk flow of the solvent-buffer mixture and electromigration of positively-charged species, both toward the negative electrode 25. The bulk flow of the solvent-buffer mixture carries the analyte in the direction of the arrow 26 out of the extraction tube 11 into the collection tube in concentrated form. The concentrated solution of analyte is then withdrawn from the collection tube for analysis.

The following examples are offered for illustrative purposes, and are intended neither to define nor to limit the invention in any manner.

EXAMPLE 1

This example illustrates the effectiveness of the present invention in the purification and concentration of cimetidine from serum. Ranitidine was included in the sera samples as an internal standard at 10 µg/mL. The cimetidine and ranitidine used in these examples were obtained from Orion Pharmaceutica, Espoo, Finland. The molecular formulas for these compounds are as follows:

Stock solutions of cimetidine and ranitidine in methanol were prepared at 5 mg/mL, and the cimetidine samples were serially diluted. Aliquots of the cimetidine (50 µL) and the ranitidine (10 µg/mL) were added to serum samples (0.5 mL).

A packed C-18 (octadecylsilane-bonded silica) cartridge was used, with internal diameter of 6 mm, packing length 0.8 cm, particle size 40 microns, packing weight 100 mg, with porous polyethylene frits (porosity 20 microns, thickness 1 mm) at both ends of the packing. The packing was conditioned and activated by injecting methanol into the column through a tuberculin syringe, followed by water and buffer. The buffer was 10 mM txis(hydroxymethyl)aminomethane ("TRIZMA"), 3.2 mM acetic acid, pH 7.7. A cimetidine-containing serum sample was diluted 1:1 (volume basis, total volume 1.0 mL) with a dilution buffer consisting of 40 mM TRIZMA and 13.0 mM acetic acid, and drawn into the cartridge. An equal volume of water, purified by distillation and ion exchange, was also drawn into the cartridge and expelled, both in the same flow direction as the loading of the sample. The water in the cartridge was then replaced with 160 µL of an elution solvent consisting of tetrahydrofuran diluted 1:1 (volume basis) in a buffer consisting of 5 mM TRIZMA, 1.7 mM acetic acid, pH 7.7, by drawing the elution solvent through the cartridge in the direction opposite that used for the sample loading and washing.

Electric leads were then mounted to the two ends of the cartridge with the negative electrode at the end through which the sample and water wash had entered. The electrodes were placed on the sides of the frits opposite the sides facing the packing, with the negative electrode sharpened and attached directly to the frit. A d.c. voltage of 150 V was then applied.

Eluate fractions were collected and aliquots of the fractions were analyzed in a capillary electrophoresis apparatus. The capillary was a fused-silica capillary measuring 60 cm (length)×50 µm I.D.×180 µm O.D., on which an on-column flow cell for UV detection had been formed by removing the polyimide coating in a small area about 15 cm from the capillary end. Prior to use, the capillary had been rinsed with water followed by 0.1M NaOH solution, then water again, then stabilized with buffer and by injecting the cimetidine stock solution as described above. Each change of buffer was preceded by a 15-minute rinse, and short rinses with buffer were performed between injections. Under the conditions used, the chromatographic process occurring in this capillary was micellar electrokinetic capillary chromatography (MECC).

Table I below summarizes the types and concentrations of the buffers used in the cartridge and in the capillary, together with the operating conditions used in each.

TABLE I

| Buffers, Solvents and Conditions Used in Example 1 | | |
|---|---|---|
| | Eluting Solvent Used in Preconcentration Cartridge | Buffer Used in Capillary |
| THF | 50% | — |
| TRIZMA | 3.7 mM | 3.3 mM |
| Acetic Acid | 1,8 mM | — |
| HTAB | — | 9.8 mM |
| NaH$_2$PO$_4$ | — | 9.4 mM |
| pH | 7.7 | 6.4 |
| Flow direction | To cathode | To anode |
| Voltage | +150 V | −20 kV |

TABLE I-continued

Buffers, Solvents and Conditions Used in Example 1

|  | Eluting Solvent Used in Preconcentration Cartridge | Buffer Used in Capillary |
|---|---|---|
| current | 0.5 mA | 11–13 µA |
| Tube Radius | 6 mm | 50 µm |

Sample injection was performed by dipping one end of the buffer-filled capillary into the eluate fraction for 10–15 seconds, while maintaining a height difference of 13.5 cm between the injection point and the buffer level. The buffer system included the cationic detergent hexadecyltrimethylammonium bromide (9.8 mM), TRIZMA base (3.3 mM) and sodium hydrogen phosphate (9.4 mM) at pH 6.4. Detection was achieved using a conventional UV detector adjusted to 228 nm.

Calibrations were performed on this system for the cimetidine:ranitidine peakheight ratios in spiked serum samples, using both 20-µL and 50-µL fraction volumes, with 5–6 dilutions for each. Data from the resulting linear regression plot are shown in Table II below.

TABLE II

Linear Regression Calibration Data for Spiked Cimetidine Serum Samples

| Range (µg/mL) | No. of Points | Correlation Coefficient | x-Axis Intercept | y-Axis Intercept | Colected Volume (µL) |
|---|---|---|---|---|---|
| 0.233–11.4 | 6 | 0.9991 | 0.126 | −0.016 | 50 |
| 0.233–11.4 | 5 | 0.9993 | 0.047 | −0.004 | 20 |

The precision and accuracy of the method were determined by performing four analyses each of 0.5-mL serum samples at two concentrations—0.47 µg/mL and 3.7 µg/mL. Precision was determined by comparing the amounts of cimetidine which had been added to the samples to the amounts determined as a result of the analysis. The peak-height ratios of cimetidine to ranitidine were also measured, and accuracy (in terms of relative error) was calculated by using the linear regression calibration graph referred to above. The results are shown in Tables III and IV below.

TABLE III

Precision and Accuracy for Spiked Serum Samples (0.47 µg/mL of Cimetidine)

|  | Cimetidine-ranitidine peak height ratio | Added (µg) | Found (µg) | Relative error (%) |
|---|---|---|---|---|
|  | 0.076 | 0.233 | 0.262 | +12.4 |
|  | 0.079 | 0.233 | 0.276 | +18.5 |
|  | 0.082 | 0.233 | 0.289 | +24.0 |
|  | 0.066 | 0.233 | 0.219 | −6.0 |
| Mean | 0.076 |  | 0.261 | +12.2 |
| Standard Deviation | 0.007 |  | 0.03 | 13 |
| Relative Standard Deviation (%) | 9.2 |  | 11.6 |  |
| No. of Samples | 4 | 4 | 4 |  |

TABLE IV

Precision and Accuracy for Spiked Serum Samples (3.7 µg/mL of Cimetidine)

|  | Cimetidine-ranitidine peak height ratio | Added (µg) | Found (µg) | Relative error (%) |
|---|---|---|---|---|
|  | 0.402 | 1.85 | 1.71 | −7.6 |
|  | 0.428 | 1.85 | 1.83 | −1.1 |
|  | 0.446 | 1.85 | 1.91 | +3.2 |
|  | 0.414 | 1.85 | 1.77 | −4.3 |
| Mean | 0.423 |  | 1.81 | −2.5 |
| Standard Deviation | 0.019 |  | 0.085 | 4.6 |
| Relative Standard Deviation (%) | 4.5 |  | 4.7 |  |
| No. of Samples | 4 |  | 4 | 4 |

According to the data in these tables, the relative standard deviation values for the peak height ratios were 9.2% for the 0.47 µg/mL fraction size and 4.5% for the 3.7 µg/mL fraction size, while the relative standard deviations for the quantitative cimetidine determinations were 11.6% and 4.7%, respectively.

The percent drug recovery achieved by the method was estimated by comparing the peak heights of cimetidine in the first eluted 20- and 50-µL fractions with a standard solution sample prepared in the eluting solvent. The recovery for the 20-µL sample was 74% (standard deviation=15%, n=4), while the recovery for the 50-µL sample was 93% (standard deviation=2%, n=4).

Figure 2A:
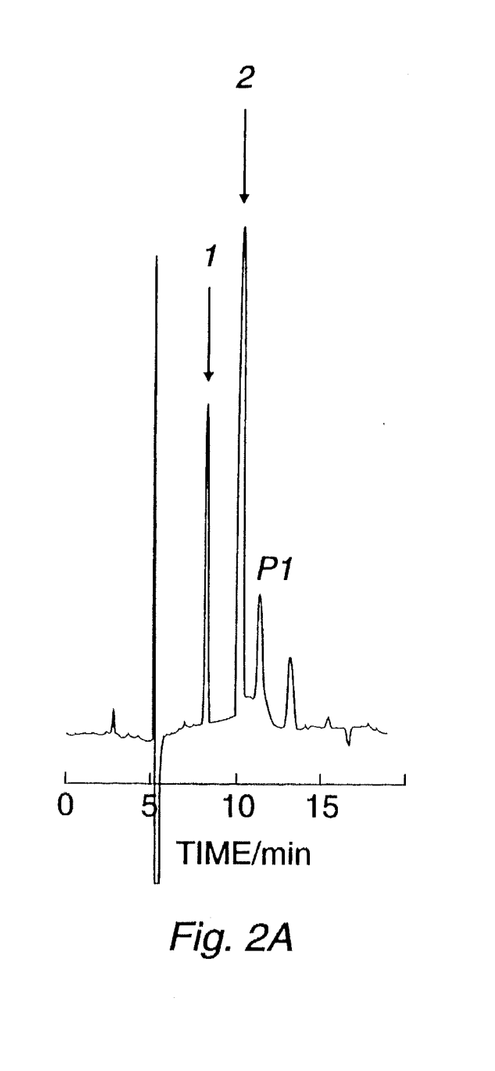
FIGS. 2A, 2B and 2C are electropherogram traces of successive eluate fractions obtained by a preconcentration procedure using the apparatus of FIG. 1.
Figure 2B:
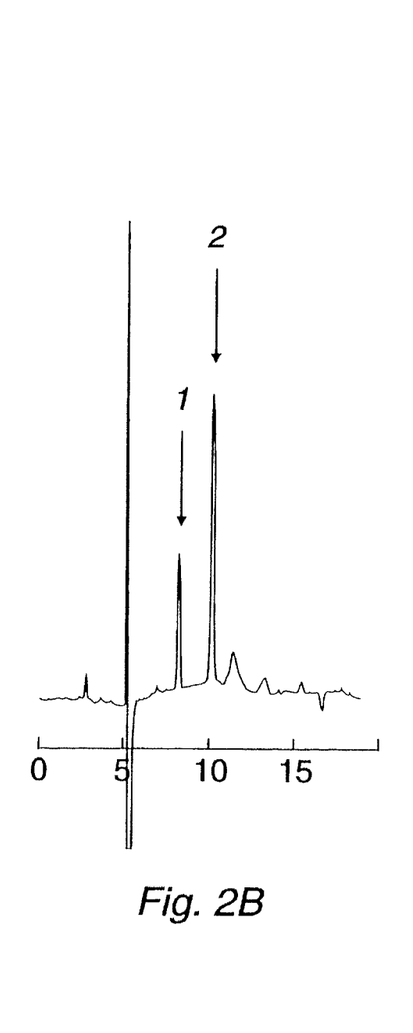
Figure 2C:
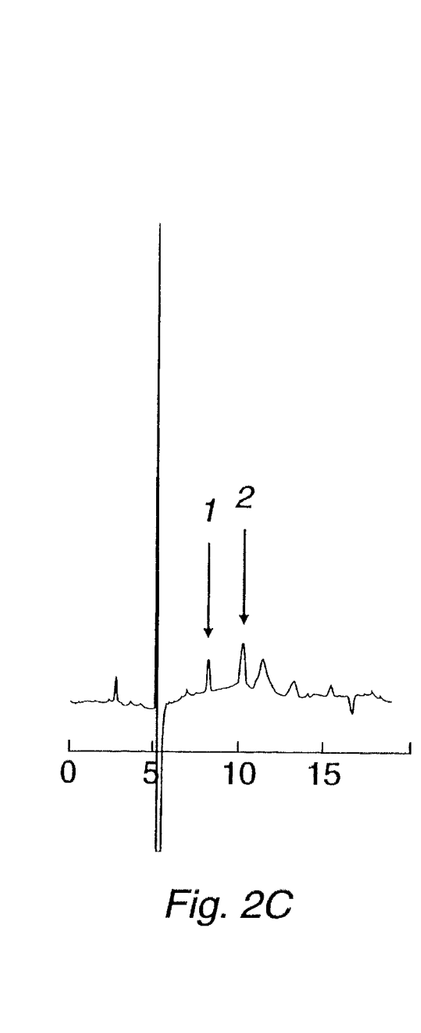

FIGS. 2A, 2B, and 2C show electropherograms taken in the capillary for three successive 20-µL sample fractions electrically eluted from the cartridge. In each electropherogram, cimetidine is identified as peak no. 1 and ranitidine as peak no. 2. The peak designated "P1" is an unknown serum background component. It is clear from these electropherograms that the bulk of the cimetidine is contained in the first two 20-µL eluate fractions.

Figure 3A:
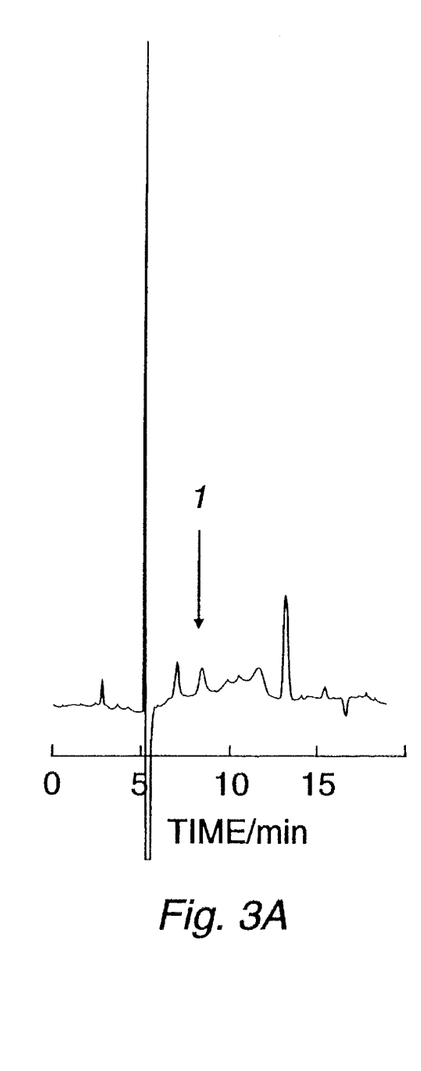
FIGS. 3A and 3B are electropherogram traces similar to those of FIGS. 2A, 2B and 2C except that FIG. 3A was taken without preconcentration, and FIG. 3B was taken without inclusion of the analyte.
Figure 3B:
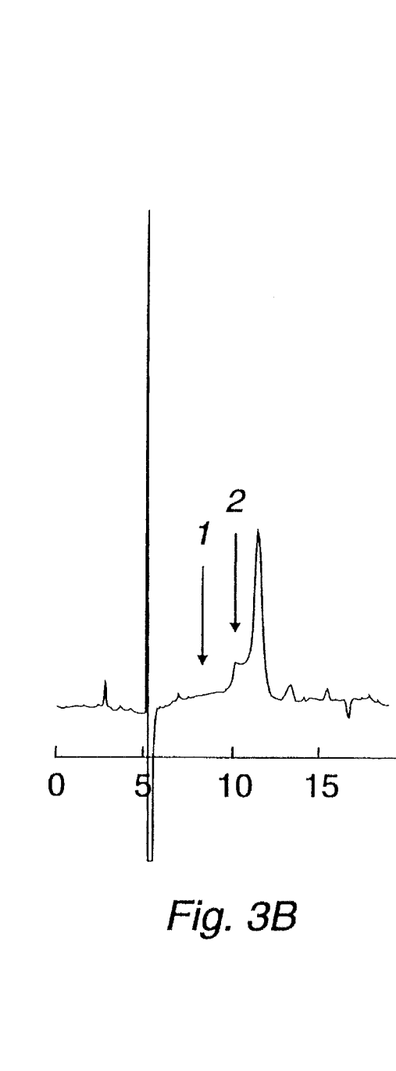

FIGS. 3A and 3B compare the cimetidine standard (11.4 µg/mL) prepared in an elution solvent mixture without preconcentration (FIG. 3A) with a blank serum extract after electrical elution from the cartridge (preconcentration) (FIG. 3B). Here as well, peak no. 1 is cimetidine and peak no. 2 is ranitidine. It is clear from this comparison that in neither case is a quantitative measurement of the cimetidine possible.

EXAMPLE 2

This example compares three solvents in tens of their effectiveness as elution buffers in the elution of cimetidine from a C-18 column. The materials and apparatus of Example 1 were used, except that the serum samples further contained rosaniline dye (an aromatic primary amine) as a marker, and three different solvents were used. Rosaniline was selected because rosaniline and cimetidine elute together and the eluting colored zones are capable of being observed visibly.

The three solvents were tetrahydrofuran, acetonitrile and methanol, and their elution strength, viscosity and polarity are shown in Table V below:

TABLE V

Properties of Solvents Used in
Electrochromatographic Measurements

| Solvent | Elution Strength[a] | Viscosity (cP) (25° C.)[b] | Dielectric Constant (20° C.)[b] |
|---|---|---|---|
| Tetrahydrofuran | 3.7 | 0.55[c] | 7.6 |
| Acetonitrile | 3.1 | 0.34 | 37.5 |
| Methanol | 1.0 | 0.55 | 32.6[d] |

[a]On octadecylsilane. Krieger, P.A., High Purity Solvent Guide, Burdick & Jackson Labs., McGaw Park, Illinois, U.S.A. (1984).
[b]Bruno, T.J., et al., eds., CRC Handbook of Basic Tables for Chemical Analysis, CRC Press, Boca Raton, Florida, U.S.A., p. 89 (1989).
[c]20° C.
[d]25° C.

Figure 4:
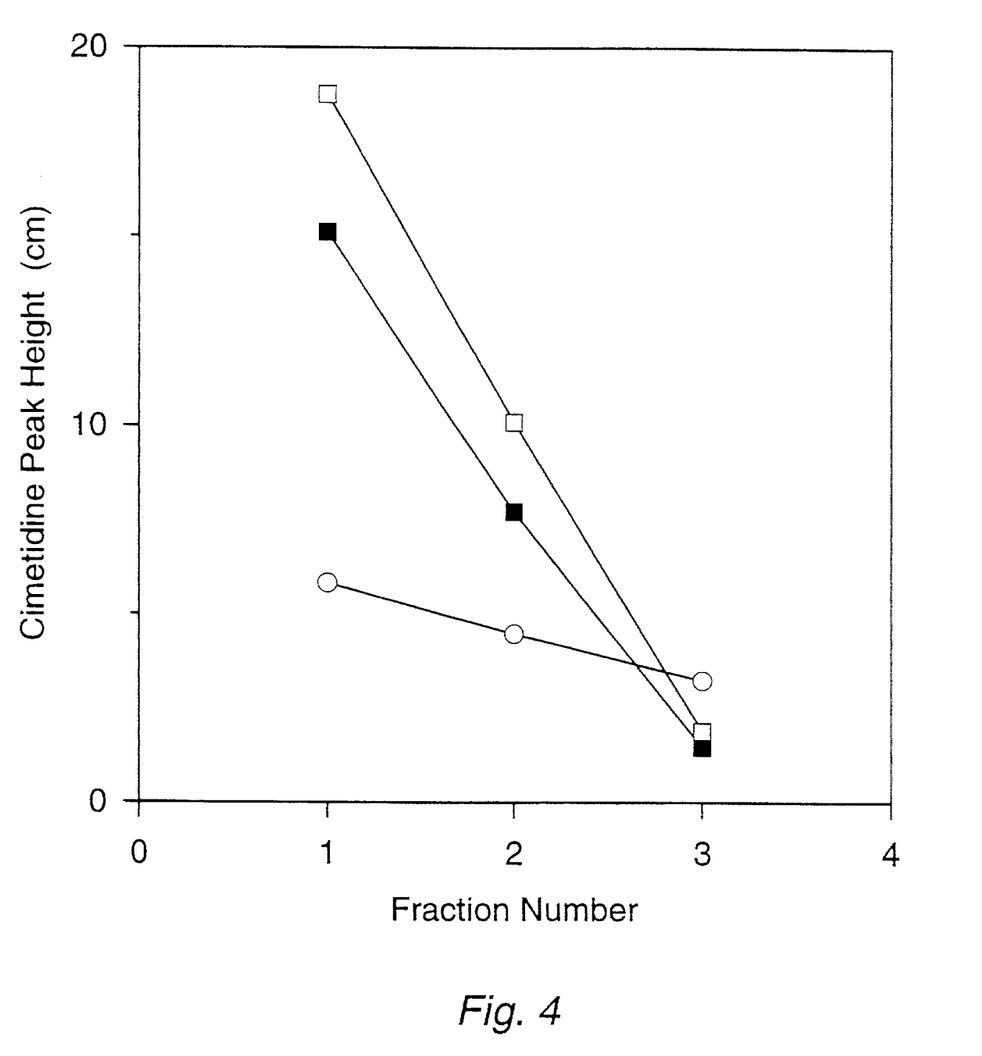
FIG. 4 is a plot of analyte peak height vs. eluate fraction taken from electropherogram traces of successive eluate fractions, and comparing different solvents used in the desorption stage.

Each solvent was tested in the preconcentration and elution procedure by first combining the solvent with an equal volume of buffer consisting of 3.7 mM TRIZMA, 1.8 mM acetic acid, pH 7.7. Conditioning of the cartridge packing, passing of the sample, washing and elution then proceeded in the manner described in Example 1, using each of the three solvent/buffer mixtures in separate experiments. Three successive 20-μL fractions were collected for each experiment, and an aliquot from each fraction was taken for electrophoretic analysis in the capillary. The cimetidine peak height was measured for each fraction, and the results are shown graphically in FIG. 4, in which each data point represents the average of 3–6 samples. Open squares in the plot represent data taken with tetrahydrofuran as the solvent; filled squares represent acetonitrile; and open circles represent methanol. The plot indicates that tetrahydrofuran, which has the lowest dielectric constant and the largest elution strength on octadecylsilane, resulted in the most effective elution medium.

EXAMPLE 3

This example illustrates the advantage of electrically-driven elution over a pressure-driven elution.

Figure 5:
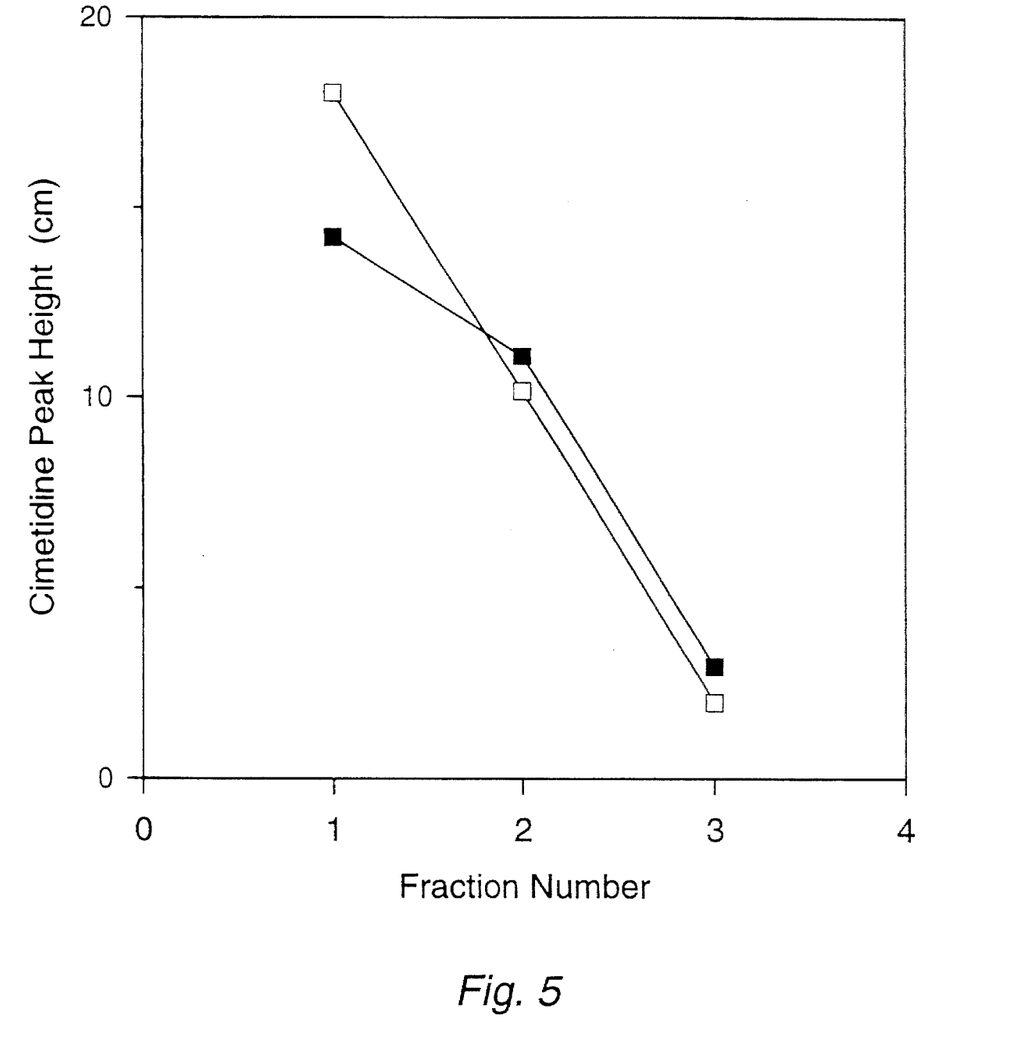
FIG. 5 is a plot of analyte peak height vs. eluate fraction taken from electropherogram traces of successive eluate fractions, and comparing the process of the invention with a process in which electroosmotic flow is replaced by pressure-driven flow.
Figure 6:
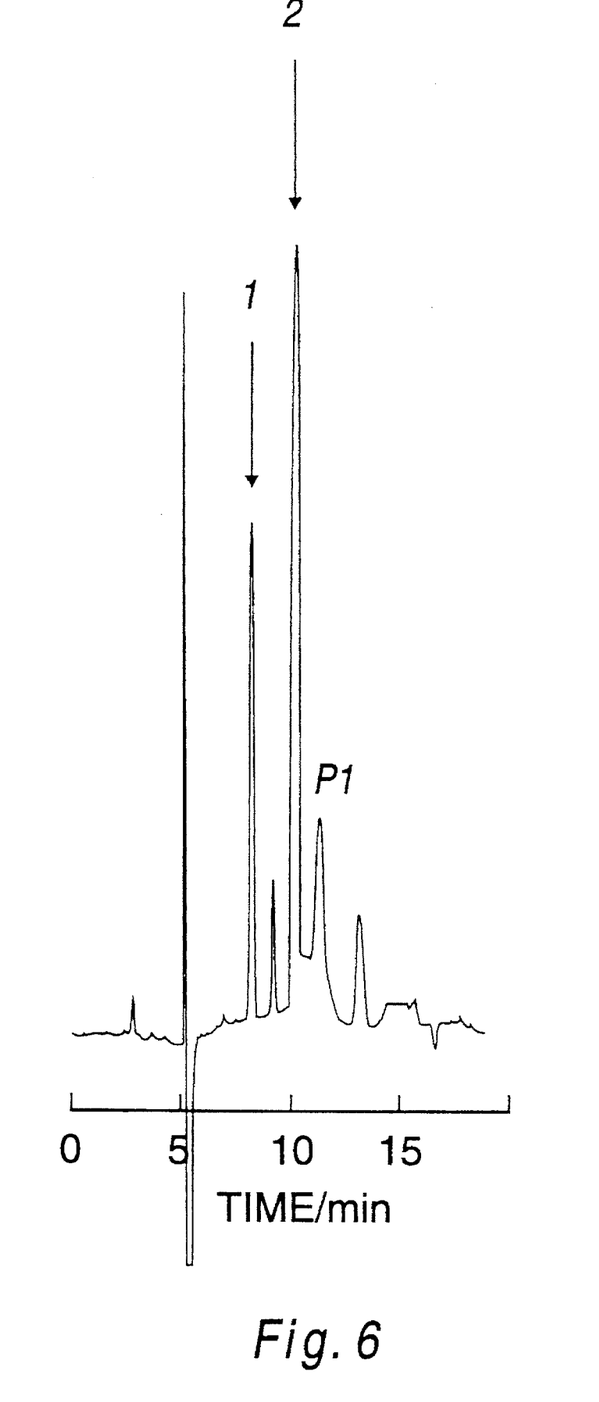
FIG. 6 is an electropherogram trace of an initial eluate fraction obtained using a method outside the scope of the present invention, with pressure-driven flow in place of electroosmotic flow. This Figure also represents the prior art.
Figure 7:
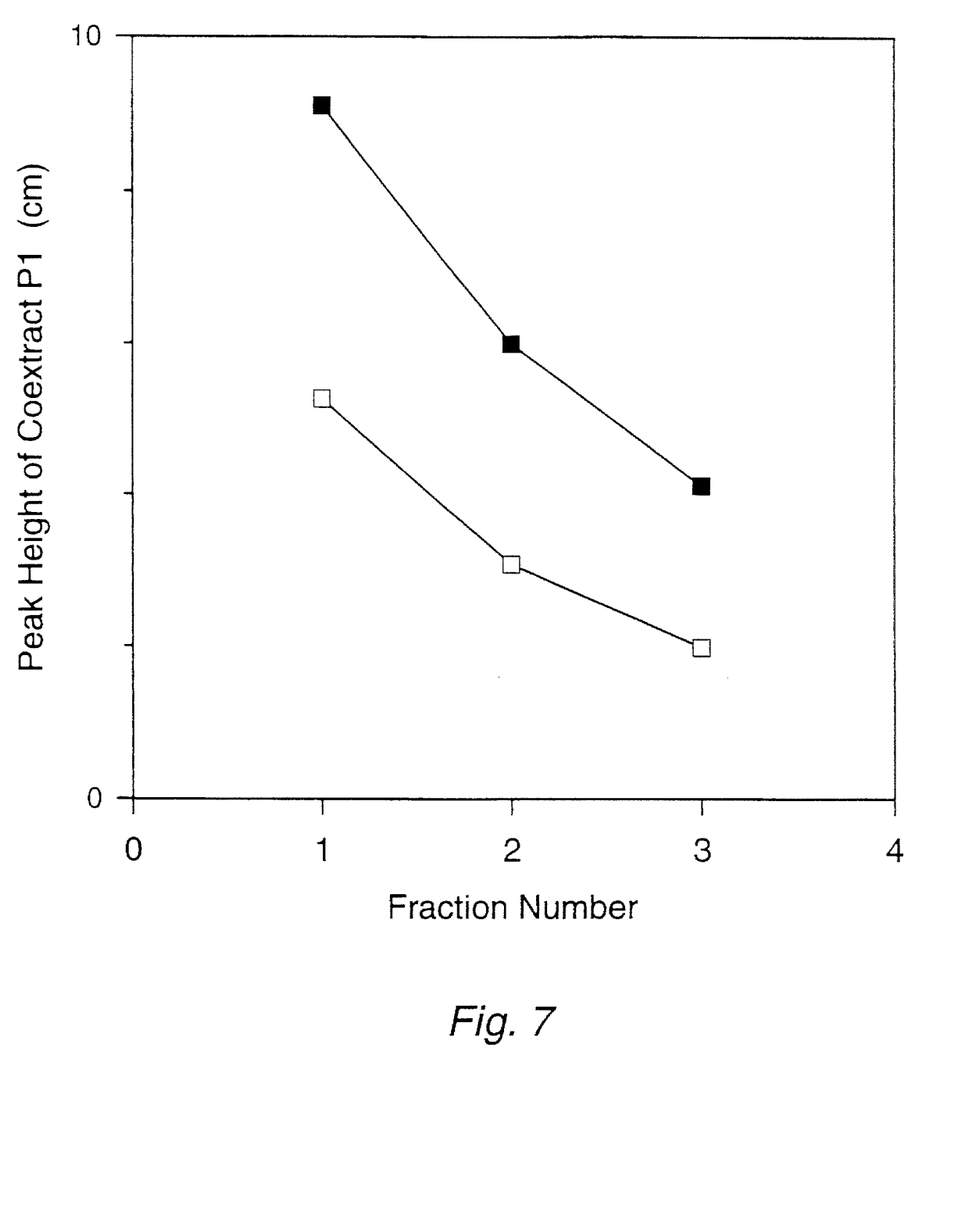
FIG. 7 is a plot of peak height vs. eluate fraction for a component other than the analyte, taken from the same electropherogram traces used in plotting FIG. 5 and addressing the same comparison.

The procedure of Example 1 was followed, and the same materials used, except that for the pressure-driven elution, a simple syringe action was used in place of the application of the voltage across the cartridge packing. The syringe action forced the flow in the same direction as the electroosmotic flow induced by the voltage in the electrically-driven elution. Repeated samples were run in this manner, and the results are shown in FIGS. 5, 6 and 7, as well as Table VI below.

TABLE VI

Concentration Factors for Cimetidine in Serum Sample:
Enrichment by Electrical (E) and Pressure (P) Elution Mode

| Solvent (50%) | Elution Mode | Concentration Factor | Standard Deviation | Number of Samples | Flow Rate (μL/min) |
|---|---|---|---|---|---|
| Tetrahydrofuran | E | 13 | 2 | 6 | 40 |
| Tetrahydrofuran | P | 8 | 2 | 5 | —[a] |
| Acetonitrile | E | 10 | 3 | 3 | 60 |
| Methanol | E | 4 | 2 | 3 | 30–60 |

[a]Not measured.

The table shows that comparison of the concentration factor for tetrahydrofuran in the electrical mode with the factor in the pressure mode indicates the advantage of the electrical mode with this solvent. Corresponding data obtained with acetonitrile and methanol as solvents are included for comparison.

In FIG. 5, cimetidine peak heights are shown for three successively eluted 20-μL fractions, the open squares representing the electrical mode and the closed squares representing the pressure mode. The plot indicates that the cimetidine elution trends were similar, but there was a substantial difference in precision. The relative standard deviation in the electrical mode, based on four samples, was 5.9%, while the relative standard deviation in the pressure mode, also based on four samples, was 18.9%.

FIG. 6 is an electrophoretic trace of the first 20-μL pressure-driveneluate. The corresponding trace for the electrically-driven eluate is shown in FIG. 2A. A comparison of the two shows the higher concentration of the unidentified serum component "P1" in the electropherogram of the pressure-driven eluate.

FIG. 7 is a peak height comparison of the "P1" serum component in the same three successively eluted 20-μL fractions for whom the cimetidine peak heights are plotted in FIG. 5. The advantage of the electrically-driven elution is evident in the lower peak heights.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A method for treating a source solution containing a suspected analyte to obtain a concentrated solution of said analyte, said method comprising:
    (a) passing said source solution through an adsorption medium retained in a column in a first direction by imposing a pressure gradient across said column in the substantial absence of a voltage gradient and under conditions promoting selective immobilization of said analyte by said adsorption medium;
    (b) imposing a voltage gradient across said column in the substantial absence of a pressure gradient to induce electroosmotic bulk flow therethrough in a second direction opposite to said first direction, under conditions promoting desorption of said analyte from said adsorption medium; and
    (c) recovering mobile phase leaving said adsorption medium due to said electroosmotic bulk flow, said mobile phase containing said analyte.

2. A method in accordance with claim 1 in which said adsorption medium is comprised of particulate solids.

3. A method in accordance with claim 1 further comprising:
    (a) passing a wash solution through said adsorption medium between steps (a) and (b) to remove therefrom solutes which chromatographically interfere with said analyte.

4. A method in accordance with claim 1 in which said suspected analyte is present in said source solution at a concentration of less than about 100 μg/mL.

5. A method in accordance with claim 1 in which said suspected analyte is present in said source solution at a concentration of less than about 50 μg/mL.

6. A method in accordance with claim 1 in which said suspected analyte is present in said source solution at a concentration of less than about 20 µg/mL.

7. A method in accordance with claim 1 in which said suspected analyte has a $pK_a$ of from about 6.5 to about 7.5, and said adsorption medium has a surface with substantially non-polar functional groups.

8. A method in accordance with claim 7 in which step (a) includes passing through said adsorption medium a first mobile phase which is substantially polar relative to said adsorption medium, and step (b) includes passing through said adsorption medium a second mobile phase of polarity substantially lower than said first mobile phase.

9. A method in accordance with claim 1 in which said conditions under which step (a) is performed differ from said conditions under which step (b) is performed at least in part by the use of different mobile phases.

10. A method in accordance with claim 9 in which step (a) includes passing a first mobile phase through said adsorption medium, and step (b) includes passing a second mobile phase through said adsorption medium, and said method further comprises filling said adsorption medium with said second mobile phase prior to said (b).

11. A method in accordance with claim 9 in which said different mobile phases differ at least in part according to degree of polarity.

12. A method in accordance with claim 9 in which step (a) includes passing a first mobile phase through said adsorption medium, and step (b) includes passing a second mobile phase through said adsorption medium, said adsorption medium having a polarity which is substantially less than the polarity or said first mobile phase.

13. A method in accordance with claim 9 in which step (a) includes passing a first mobile phase through said adsorption medium, and step (b) includes passing a second mobile phase through said adsorption medium, said adsorption medium having a polarity which is substantially less than the polarity of said first mobile phase, and said second mobile phase having a polarity which is substantially less than the polarity of said first mobile phase.

* * * * *